(12) United States Patent
Shafer et al.

(10) Patent No.: US 10,371,574 B2
(45) Date of Patent: *Aug. 6, 2019

(54) DETECTOR DEVICE FOR DETECTION OF A SPECTRAL PORTION FOR A MICROSCOPE

(71) Applicant: Carl Zeiss Microscopy GmbH, Jena (DE)

(72) Inventors: David Shafer, Fairfield, CT (US); Tiemo Anhut, Jena (DE); Matthias Wald, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/170,931

(22) Filed: Oct. 25, 2018

(65) Prior Publication Data

US 2019/0063993 A1 Feb. 28, 2019

Related U.S. Application Data

(63) Continuation of application No. 15/524,119, filed as application No. PCT/EP2015/075811 on Nov. 5, 2015, now Pat. No. 10,132,685.

(30) Foreign Application Priority Data

Nov. 17, 2014 (DE) .................. 10 2014 116 782

(51) Int. Cl.
*G01J 3/28* (2006.01)
*G01J 3/44* (2006.01)
(Continued)

(52) U.S. Cl.
CPC ............ *G01J 3/4406* (2013.01); *G01J 3/021* (2013.01); *G01J 3/0208* (2013.01); *G01J 3/14* (2013.01);
(Continued)

(58) Field of Classification Search
CPC ........ G01J 3/28; G01J 3/02; G01J 3/14; G01J 3/18; G01J 3/10; G01J 3/36; G01N 21/64; G02B 21/36; G02B 21/16; G02B 27/00
See application file for complete search history.

(56) References Cited

U.S. PATENT DOCUMENTS

| 4,193,691 A | 3/1980 | Fjarlie |
| 4,890,901 A | 1/1990 | Cross |

(Continued)

FOREIGN PATENT DOCUMENTS

| DE | 19842288 A1 | 2/2000 |
| DE | 102004058833 A1 | 6/2006 |

(Continued)

*Primary Examiner* — Abdullahi Nur
(74) *Attorney, Agent, or Firm* — Murphy, Bilak & Homiller, PLLC (57) ABSTRACT

A detection device for a microscope comprises a dispersive element in the beam path of light and a selection element. The selection element separates a beam path of a spectral portion of the light from the beam path of the light. The detector device furthermore comprises a focusing optical unit configured to focus the beam path of the spectral portion of the light onto a sensor. By way of example, the microscope may be a confocal microscope.

16 Claims, 6 Drawing Sheets

(51) Int. Cl.
  *G01J 3/02* (2006.01)
  *G01J 3/14* (2006.01)
  *G01J 3/36* (2006.01)
  *G02B 21/00* (2006.01)
  *G01N 21/64* (2006.01)
  *G02B 27/10* (2006.01)
  *G02B 27/12* (2006.01)
  *G01J 3/18* (2006.01)
  *G02B 21/16* (2006.01)
  *G02B 21/36* (2006.01)
  *G02B 27/00* (2006.01)

(52) U.S. Cl.
  CPC . *G01J 3/18* (2013.01); *G01J 3/36* (2013.01); *G01N 21/6458* (2013.01); *G02B 21/0064* (2013.01); *G02B 21/0076* (2013.01); *G02B 21/16* (2013.01); *G02B 21/361* (2013.01); *G02B 27/0025* (2013.01); *G02B 27/1013* (2013.01); *G02B 27/126* (2013.01); *G01N 2021/6421* (2013.01); *G01N 2201/068* (2013.01)

(56) References Cited

U.S. PATENT DOCUMENTS

| | | |
|---|---|---|
| 5,504,575 A | 4/1996 | Stafford |
| 6,255,646 B1 | 7/2001 | Shimada |
| 10,132,685 B2 * | 11/2018 | Shafer .................. G01J 3/4406 |
| 2001/0046046 A1 | 11/2001 | Schoeppe |
| 2005/0174425 A1 | 8/2005 | Harris |
| 2011/0216316 A1 | 9/2011 | Moser et al. |
| 2013/0077086 A1 | 3/2013 | Chuang et al. |

FOREIGN PATENT DOCUMENTS

| | | |
|---|---|---|
| DE | 102009006728 A1 | 8/2010 |
| DE | 102009043745 A1 | 4/2011 |
| EP | 0717834 B1 | 4/2001 |
| EP | 1053497 B1 | 3/2002 |
| JP | H02502588 A | 8/1990 |
| JP | 2000056233 A | 2/2000 |
| JP | 2002530716 A | 9/2002 |

* cited by examiner

DETECTOR DEVICE FOR DETECTION OF A SPECTRAL PORTION FOR A MICROSCOPE

RELATED APPLICATIONS

This application is a continuation of U.S. application Ser. No. 15/524,119 filed 3 May 2017, which is a U.S. National Phase Application of PCT/EP2015/075811 filed 5 Nov. 2015, which claims foreign priority to German Application No. DE102014116782.1 filed 17 Nov. 2014. The entire contents of each aforementioned application is incorporated herein by reference.

TECHNICAL FIELD

Various embodiments of the invention relate to a detector device for a microscope. In particular, various embodiments of the invention relate to a detector device which comprises a focusing optical unit arranged in the beam path of a spectral portion of light and configured to focus the beam path of the spectral portion of the light onto a sensor.

BACKGROUND

In microscopy, there is a need for particularly high sensitivities of sensors for generating signals. In this way, an imaging quality may improve. Conventional large-area detectors, such as e.g. photomultipliers (PMTs), have a quantum efficiency of approximately 20%-50%, provided that these are, for example, implemented by means of GaAsP anodes. Such detectors have comparatively large sensitive areas (detection area) of the order of several mm2 or several tens of mm2.

In principle, sensors with a relatively high sensitivity are known. By way of example, avalanche photodiodes (APDs) and other silicon-based sensors which have a comparatively high quantum efficiency of e.g. 80-90% are known. Typically, this is obtained by way of a comparatively small detection area which, for example, may be circular with a diameter of approximately 100 µm. This corresponds to a detection area of the order of less than 0.05 mm2.

Confocal microscopy is a specific type of microscopy. Here, a portion of a specimen is typically illuminated and this illuminated portion is varied incrementally in various illumination steps. By way of example, a laser-scanning microscope (LSM) may be used to this end. A light intensity of the light reflected by the specimen or otherwise emitted, e.g. by way of fluorescence, may be detected by a corresponding detector device for each illumination step.

The detection of emitted light in a spectrally selective manner is known within the scope of confocal microscopy. This is necessary, particularly in fluorescence-based confocal microscopy. As a result, a particularly high information content may be obtained during imaging. By way of example, the spectrally sensitive detection may be achieved by the use of optical filters. The optical filters suppress a specific spectral portion more strongly than other spectral portions. By way of example, the optical filters may be tuned to a specific wavelength or embodied as a so-called graduated filter. However, the use of optical filters typically attenuates the intensity of the light, as a result of which a signal level is reduced. As a result, there may in turn be a reduction in the signal-to-noise ratio in the measured signal. This may reduce an accuracy of the measurement.

A further option for suppressing specific spectral portions for a spectrally selective detection is offered by the spatial-spectral decomposition of the light with a subsequent manipulation of the spectral components as desired; in this respect, see e.g. the publication DE 198 42 288 A1. Techniques in which the beam path of individual spectral portions of the light may be manipulated by way of mirrors are known; in this respect, see e.g. the publications EP 0 717 834 B1, EP 1 053 497 B1 and U.S. Pat. No. 6,255,646 B1.

The use of mirrors may be comparatively complicated and expensive. Further, such techniques are disadvantageous in that a selection of individual spectral portions of the light is effected in the collimated beam. This typically limits a spectral resolution.

SUMMARY

Therefore, there is a need for an improved detector device for a microscope. In particular, there is a need for such a detector device which remedies at least some of the disadvantages specified at the outset. In particular, there is a need for a detector device which is configured for spectrum-selective detection and which uses small-area sensors with a high sensitivity. Moreover, there is a need to be able to use small-area pixelated sensors in confocal microscopes for the purposes of the spectral detection.

This object is achieved by the features of the independent claims. The dependent claims define embodiments.

In accordance with one aspect, the present invention relates to a detector device for a microscope. The detector device is configured for selective detection of a spectral portion of light from a specimen region of the microscope. The detector device comprises a dispersive element in a beam path of the light. The detector device furthermore comprises a selection element. The selection element is arranged downstream of the dispersive element in the beam path of the light in such a way that it separates a beam path of the spectral portion of the light from the beam path of the light. The detector device furthermore comprises a focusing optical unit. The focusing optical unit is arranged downstream of the selection element in the beam path of the spectral portion of the light. The focusing optical unit is configured to focus the beam path of the spectral portion of the light onto a sensor. The detector device furthermore comprises the sensor arranged downstream of the focusing optical unit in the beam path of the spectral portion of the light.

By way of example, the microscope may be a confocal microscope. By way of example, the detector device may be arranged downstream of an illumination device of the confocal microscope and downstream of a specimen in the beam path of the light. By way of example, the detector device may furthermore comprise a pinhole arranged upstream of the dispersive element in the beam path of the light. However, the pinhole may be expendable. By way of example, the light from the specimen region of the microscope may be light reflected by the specimen and/or light emitted by the fluorescing specimen.

Thus, the detector device may facilitate a spectrally selective detection of the light by virtue of separately focusing the beam path of the spectral portion onto the sensor. A plurality of spectral portions may be detected selectively. By way of example, two, three, four or more spectral portions may be detected selectively. To this end, it may be possible for the detector device in accordance with the aspect discussed here to comprise a plurality of separation elements. By way of example, the detector device may comprise an associated separation element for each spectral portion to be separated.

By way of example, the dispersive element may be a prism or a grating. Thus, the dispersive element may bring about a spectral decomposition of the beam path of the light. In the process, the light is decomposed into the spectral components thereof; i.e., different colors are influenced differently. As a result the different spectral components are spatially spread within the beam path of the light. By way of example, the spectral portion may denote a specific spectral band. The spectrally sensitive detection may be obtained by this spectral decomposition and subsequent selection of the spectral portion by the selection element.

The spectral decomposition typically produces a comparatively large optical extent. The optical extent is often also referred to as etendue. It typically measures the extent of a beam in geometric optics. It typically contains the product of beam cross section and maximum possible solid angle. Then, it may be possible to obtain focusing on the sensor by means of the focusing optical unit despite the comparatively high etendue; expressed differently, it is possible to generate a spatially greatly delimited focal spot.

It is possible for the sensor to have a sensitive area in the region of more than 0.1 mm$^2$ or more than 1 mm$^2$ or more than 100 mm$^2$. However, in various embodiments, it is also possible to obtain focusing on a comparatively small sensor. By way of example, the sensor may have a sensitive area of less than 0.1 mm$^2$. Preferably, the sensor may have a sensitive area of less than 0.05 mm$^2$. Particularly preferably, the sensor may have a sensitive area of less than 0.02 mm$^2$. By way of example, the focusing optical unit may be configured to focus the beam path of the spectral portion of the light onto the sensitive area or detection area of the sensor. Thus, the focal spot may have substantially the same dimensions as the sensitive area of the sensor. As a result, use may also be made of those sensors which have a comparatively high sensitivity, e.g. APDs, APD arrays or single photon avalanche diode (SPAD) array sensors, electron multiplying charge-coupled device (EMCC) sensors, etc. The imaging quality may be improved.

In particular, there may be a spatially resolved detection of the point spread function—even in the case of sensors with a comparatively small sensor area. Thus, the sensor may comprise a plurality of pixels or be a pixelated sensor. This allows a detection with an improved sensitivity and resolution, as well as further functions such as e.g. a digital pinhole function. As a result, it may be possible to measure the imaged focal distribution in a spatially resolved manner. By way of example, use may be made of an SPAD sensor; by way of example, the SPAD sensor may comprise 100× 100 pixels; in such a scenario, the sensitive area may have dimensions of the order of e.g. 10×10 mm$^2$.

In particular, what, may be obtained by means of the techniques described herein is that diffraction-limited imaging of the pinhole on the sensor is achieved. This means that an image of the pinhole on the sensor area is smaller than a central Airy disk.

What may be achieved by the provision of the dispersive element in the beam path upstream of the selection element is that a particularly high spectral resolution is achieved. The edge steepness of the selected spectral bands may be particularly high. It may also be possible for particularly thin spectral bands to be selected. The high spectral resolution may be achieved by virtue of separation of the beam path of the spectral portion of the light taking place where a decomposition of the beam path into the carious spectral components has taken place, i.e. in a spectrally resolved plane. It would be possible for the detector device to comprise an imaging optics, such as e.g. a lens, arranged between the dispersive element and the selection element in the beam path of the light. By way of example, the imaging optics may bring about focusing of the beam path of the light into a focal plane. By way of example, the selection element, may be arranged in the focal plane or close to the focal plane. Typically, the spectral resolution for the selection may be increased if the selection element is situated within the depth of field of the focal plane.

The selection element may selectively influence that spatial region of the beam path of the light which corresponds to the spectral portion. By way of example, the selection element may be arranged in the beam path of the light in such a way that the spectral components of the spectral portion of the light are optically influenced or selected by the selection element while other spectral components of the light are not optically influenced or selected by the selection element.

By way of example, the selection element may comprise at least one prism. By way of example, the at least one prism may be wedge-shaped. By way of example, at least one of the at least one prisms may partly protrude into the beam path of the light. As a result of this, a different spectral portion may be selected and the corresponding beam path may be separated depending on the position of the at least one prism in the beam path of the light.

In general, the configuration of the focusing optical unit is not particularly restricted. By way of example, the focusing optical unit could comprise mirrors and/or lenses. By way of example, the focusing optical unit may furthermore comprise a transverse chromatic aberration correction element arranged in the beam path of the spectral portion of the light. By way of example, the transverse chromatic aberration correction element may comprise at least one further wedge-shaped prism. The selection element and the transverse chromatic aberration correction element may be arranged relative to one another in such a way that a transverse chromatic aberration of the at least one prism of the selection element counteracts a further transverse chromatic aberration of the at least one prism of the transverse chromatic aberration correction element. By way of example, the transverse chromatic aberration may be caused by the selection element on account of the different path length of the various spectral components of the light through the at least one wedge-shaped prism (glass path). Thus, expressed differently, the transverse chromatic aberration correction element may reduce or compensate the transverse chromatic aberration caused by the selection element.

By way of example, it may be possible for the at least one wedge-shaped prism of the selection element and the at least one wedge-shaped prism of the transverse chromatic aberration correction element to be arranged complementary to one another with respect to the beam path of the spectral portion of the light. By way of example, arranged in a complementary manner may mean that the various spectral components of the light overall substantially pass through the same glass paths through the at least one of prism of the selection element and the at least one prism of the transverse chromatic aberration correction element. By way of example, this may be achieved by virtue of the at least one prism of the selection element and the at least one prism of the transverse chromatic aberration correction element protruding perpendicularly into the beam path of the spectral portion of the light from different directions and/or said prisms being oriented rotated through 180° in relation to one another about an axis of symmetry of the prism. By way of example, it is possible that the at least one prism of the selection element and the at least one prism of the transverse chromatic aberration correction element protrude into the beam path of the spectral portion of the light from substantially opposite directions.

Alternatively, or additionally, it may be possible for the at least one prism of the selection element and the at least one prism of the transverse chromatic aberration correction element to have substantially the same optical properties. By way of example, a material of the at least one prism of the selection element may correspond to a material of the at least one prism of the transverse chromatic aberration correction element. By way of example, the materials of the at least one prism of the selection element and of the at least one prism of the transverse chromatic aberration correction element may have the same optical refractive indices or may be identical. It is also possible for a wedge angle of the at least one prism of the selection element to correspond to a wedge angle of the at least one prism of the transverse chromatic aberration correction element.

By means of such techniques described above, it is possible to achieve a particularly good reduction in the transverse chromatic aberration. As a result, it is possible to obtain particularly good focusing of the beam path of the spectral portion of the light onto the detection area of the sensor. In particular, it is possible to prevent the focal spot of the light from being laterally displaced in the sensor plane of the sensor for different spectral components of the light; it is possible to obtain a focal spot which comprises all spectral components of the spectral portion. Since use is typically made of sensors with comparatively small sensor areas, this can prevent individual spectral components of the light no longer being arranged on the sensitive area of the sensor. It is possible to achieve a virtually diffraction-limited image of the point spread function with defined spectral components on the sensor.

Having a flexibly selectable spectral portion may be a goal worth pursuing. By way of example, this may serve to produce spectral separation. To this end, provision may be made of a drive unit. The drive unit may be configured to position the selection element in a displaceable manner in the beam path. In particular, positioning of the selection element may take place at various positions perpendicular to the beam path. What this may achieve is that a different spectral portion is selected depending on the position of the selection element in the beam path—and the corresponding beam path is separated. By way of example, it would be possible for the selection element to comprise a pair of prisms which—depending on the position of the selection element protrude into the beam path of the light from substantially opposite directions. Then, a different edge region of the spectrum may be selected as spectral edge region in each case by displacing the pair of prisms. By way of example, an upper (lower) prism of the pair of prisms may be positioned in the beam path of the light and a lower (upper) prism of the pair of prisms may be positioned outside of the beam path of the light, as a result of which a red (blue) edge region of the spectrum is selected as spectral portion; as a result, the red (blue) edge region of the spectrum and the remaining spectrum of the light may be separated. Then, respectively different spectral portions may be selected by the displaceable positioning, of the selection element.

The drive unit may also be configured to position the transverse chromatic aberration correction element in a displaceable manner in the beam path of the spectral portion of the light. The drive unit may be configured to position the selection element and the transverse chromatic aberration correction element in a coupled manner. In particular, positioning of the transverse chromatic aberration correction element may take place at various positions perpendicular to the beam path. By way of example, coupled positioning may mean: displacing the selection element by a predetermined length and also displacing the transverse chromatic aberration correction element by the predetermined length. The displacement may be carried out in such a way that the glass path for a specific spectral component of the light does not change, or does not change significantly, depending on the position of the selection element.

The coupled positioning of the selection element and of the transverse chromatic aberration correction element may ensure that the transverse chromatic aberration is comparatively small—even if the selection element is displaced and positioned at different positions in the beam path for the purposes of selecting various spectral portions.

Thus, the aforementioned techniques may reduce the transverse chromatic aberration even for a flexible selection of the spectral portion and hence may prevent the focal spot from being arranged at different points—depending on the position of the selection element—with respect to a sensitive area of the sensor.

The focusing optical unit may furthermore comprise a collecting element arranged upstream of the sensor in the beam path of the spectral portion of the light. The collecting element may be at least one of a prism and a grating. By way of example, if the dispersive element is configured as a prism (grating), the collecting element may equally be configured as a prism (grating). Here, it is possible for the dispersive element and the collecting element to have substantially complementary optical properties. As described above, the dispersive element may bring about a spectral decomposition of the beam path of the light. Accordingly, it is possible for the collecting element to bring about a spectral unification of the beam path of the spectral portion of the light. By way of example, the collecting element may also be referred to as compensation prism. By way of the collecting element, it may be possible to collect the split apart spectral components of the light in the beam path of the spectral portion of the light and reduce the etendue hack to an initial dimension at the pinhole. As a result, it is possible to obtain the particularly small focal spot for the selected spectral portion.

The detector device may furthermore comprise an imaging optics. The imaging optics may be arranged at least in part between the dispersive element and the collecting element in the beam path of the light and in the beam path of the spectral portion of the light. The imaging optics may be configured to obtain optical imaging of the dispersive element onto the collecting element. Here, the imaging scale of the optical image may vary. Depending on the imaging scale, it may be necessary to modify optical properties of the collecting element in relation to the optical properties of the dispersive element. By way of the optical imaging, it may be possible to obtain a unification or collection of the previously split apart spectral components of the light in a particularly good manner. This renders particularly good focusing onto the sensitive area of the sensor possible.

By way of example, the focusing optical unit may comprise an astigmatism correction unit. The astigmatism correction unit may be configured to reduce an astigmatic aberration of the beam path of the spectral portion of the light. Thus, it is possible that a significant astigmatic aberration is introduced into the imaging on the sensor by the provision of the selection element and, optionally, the transverse chromatic aberration correction element. By way of example, the astigmatism correction unit may comprise a tilted plane parallel plate and/or one or more decentered lenses for compensating the astigmatic aberration.

Thus, what was explained above is that the focusing unit may comprise different elements, e.g. the transverse chromatic aberration correction element and/or the collecting element and/or the astigmatism correction unit. In general, the focusing unit may comprise individual elements thereof or all of these elements. By way of example, techniques were described above, in which the selection element separates the beam path of the spectral portion of the light from the beam path of the light. By way of example, the spectral portion of the light may in this case denote that spectral portion of the light which is optically influenced by the selection element. It is also possible for the spectral portion of the light to denote that spectral portion of the light which is not optically influenced by the selection element; in particular, provision of the transverse chromatic aberration correction element may be dispensed with in such a case, as an optical aberration caused by the selection element may then be particularly small or disappear.

Further, techniques were explained above, in which the selection element selects the spectral portion of the light. As a result, the spectral portion and a spectral portion complementary to the spectral portion are obtained. In general, it is possible to select two or more spectral portions. Thus, the selection element may, for example, be arranged in the beam path of the light in such a way that it separates a beam path of a further spectral portion of the light from the beam path of the light. The detector device may comprise a further focusing optical unit which is arranged downstream of the selection element in the beam path of the further spectral portion of the light. The further focusing optical unit may be configured to focus the beam path of the further spectral portion of the light onto a further sensor. The detector device may furthermore comprise the further sensor. The further sensor may be arranged downstream of the further focusing optical unit in the beam path of the further spectral portion of the light.

Thus, in general, it is possible for more than one spectral portion to be selected by the selection element. As a result, spectrally selective imaging for different spectral portions of the light may be effected comparatively quickly. It is possible for the focusing optical unit and the further focusing optical unit to be configured accordingly. As a result, it may be possible to obtain effects for the further focusing optical unit, which effects may be obtained for the focusing optical unit as described above.

In accordance with a further aspect, the present invention relates to a confocal microscope which comprises a detector device in accordance with a further aspect of the present invention.

The features set out above and features that are described below may be used not only in the corresponding combinations explicitly set out, but also in further combinations or in isolation, without departing from the scope of protection of the present invention.

BRIEF DESCRIPTION OF THE DRAWINGS

The above-described properties, features and advantages of this invention and the way in which they are achieved will become clearer and more clean understood in association with the following description of the exemplary embodiments which are explained in greater detail in association with the drawings.

DETAILED DESCRIPTION

The present invention is explained in greater detail below on the basis of preferred embodiments with reference to the drawings. In the figures, identical reference signs denote identical or similar elements. The figures are schematic representations of different embodiments of the invention. Elements depicted in the figures are not necessarily depicted true to scale. Rather, the different elements illustrated in the figures are reproduced in such a way that their function and general purpose become comprehensible to the person skilled in the art. Connections and couplings between functional units and elements as depicted in the figures may also be implemented as indirect connection or coupling. A connection or coupling may be implemented in a wired or wireless manner. Functional units may be implemented as hardware, software or a combination of hardware and software.

Below, a detector device for selecting one or more spectral portions is illustrated. By way of example, the selection is carried out by means of a wedge-shaped prism and carried out for focusing the spectral portion deflected by means of the wedge-shaped prism onto a comparatively sensitive sensor having a comparatively small sensitive area. These techniques permit focusing onto a comparatively small area after a spatially spectral split and permit a suitable optical manipulation of the beam path.

The detection device comprises means for spectral decomposition or a dispersive element. By way of example, the dispersive element may comprise a prism and/or a grating. The detection device further comprises a selection element which, for example, comprises one or more wedge-shaped prism pairs. The selection element serves for the spectral selection of the spectral portion. Further, the detection device comprises a focusing optical unit for focusing the beam path of the spectral portion on the sensor. By way of example, the focusing optical unit comprises means for spectral unification as a collecting element. By way of example, the collecting element may comprise a prism and/or a grating. The detection device comprises one or more sensors, depending on how many spectral portions are selected.

Below, reference is made, in particular, to a confocal microscope 100; cf. FIG. 1. However, in general, it is possible for the techniques according to the invention to find use in very different types of microscopes, e.g., in particular, in confocal systems such as point-confocal and line-confocal systems.

Figure 1:
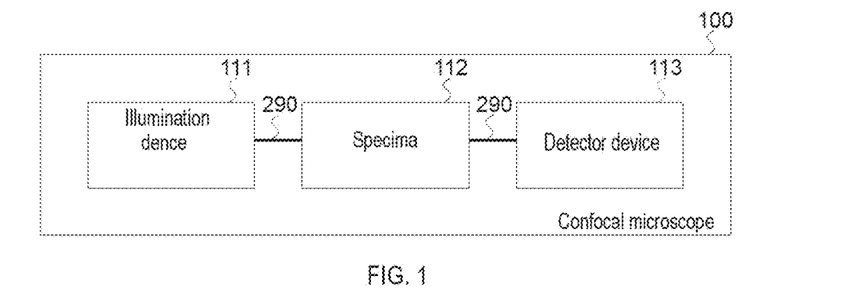
FIG. 1 is a schematic view of a confocal microscope comprising a detector device in accordance with various embodiments.

It is clear from FIG. 1 that the confocal microscope comprises an illumination device 111. By way of example, the illumination device may comprise a laser, a scanning objective with scanner, a focusing optical unit, a tube lens, etc. In general, a person skilled in the art is aware of the structure of the illumination device 111, and so no details in this respect need to be explained here.

The illumination device 111 produces a beam path 290 of the light. The specimen 112 is arranged in the beam path 290 of the light. The specimen 112 reflects light and/or fluoresces. The corresponding beam path 290 of the light is fed in turn to the detector device 113 downstream of the specimen 112. The detector device 113 comprises a sensor (not shown in FIG. 1), as a result of which imaging of the specimen 112 is rendered possible.

Figure 2:
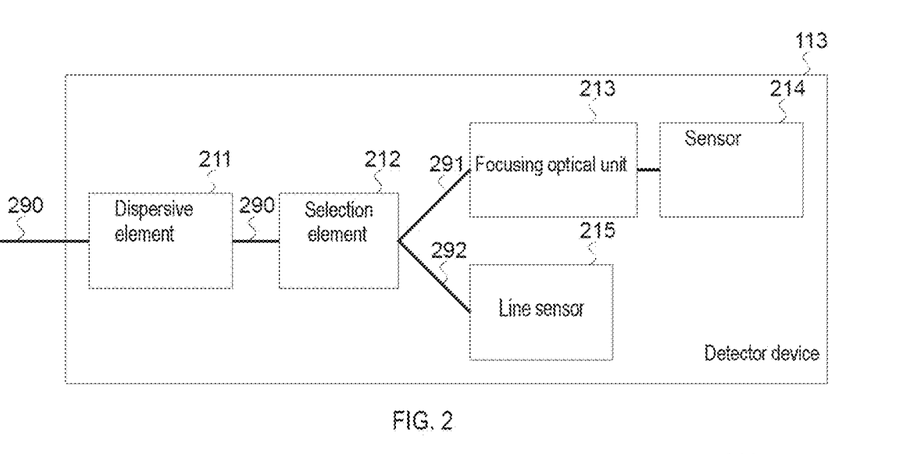
FIG. 2 is a schematic view of the detector device of FIG. 1 in greater detail, with the detector device comprising a selection element and a focusing optical unit.

FIG. 2 explains the detector device 113 in more detail. In the sequence along the beam path 290, proceeding from the specimen 112, the detector device 113 comprises a dispersive element 211, a selection element 212, a focusing optical unit 213 along a beam path 291 of a specific spectral portion of the light and a sensor 214, and along a beam path 292 of a further spectral portion—a line sensor 215. By way of example, the line sensor may be a conventional PMT sensor, in particular a multi-anode PMT. Instead of the line sensor 215, the detector device 113 could also comprise a further focusing, optical unit and a further sensor (both not shown in FIG. 2).

By way of example, the dispersive element 211 may be at least one of a prism and a grating. The dispersive element 211 provides a spectral decomposition of the beam path 290 of the light. As a result, there is a spatial spread of the various spectral components. The etendue increases. The selection element 212 is arranged downstream of the dispersive element 211 in the beam path 290 of the light in such a way that it separates the beam path 291 corresponding to the specific spectral portion of the light from the beam path 290 of the light. Separating the beam path 291 of the spectral portion may mean: splitting off the beam path 291 of the spectral portion such that the beam path 291 of the spectral portion has well-defined edges with a vanishing intensity. Then, the beam path 291 of the spectral portion may be optically modified and, in particular, focused separately. FIG. 2 shows a scenario in which the beam path 290 of the light is split into the two beam paths 291, 292. These beam paths 291, 292 correspond to different spectral portions of the light. However, it would also be possible for the beam path 290 to be split into more than two beam paths, e.g. into three beam paths (not shown in FIG. 2).

The selection element 212 may be configured in very different ways. By way of example, the selection element 212 may comprise an angled mirror/roof mirror (not shown in FIG. 2). By way of example, the angled mirror may partly protrude into the beam path 290 of the light. Only some of the beam path 290 of the light then is incident on the angled mirror and optically influenced by the angled mirror as a result. Since the angled mirror is situated downstream of the dispersive element 211 in the beam path 290 of the light, this spatial part of the beam path 290 corresponds to a specific frequency range of the spectrum of the tight. As a result, it is possible to select an edge region of the spectrum as spectral portion.

By way of example, the selection element 212 could also comprise at least one wedge-shaped prism; by way of example, the selection element 212 may comprise a pair of wedge-shaped prisms. By way of example, one of the two wedge-shaped prisms may protrude into the beam path 290 of the light—depending on the position of the pair of wedge-shaped prisms perpendicular to the beam path—and thus select the spectral portion of the light. Here, the spectral portion is selected in a manner analogous to the above-described implementation using a angled mirror.

The focusing optical unit 213 is configured to focus the beam path 291 of the specific spectral portion of the light onto the sensor 214. To this end, the focusing optical unit 213 focuses the beam path of 291 onto a comparatively small-area focus, wherein the focus is positioned on a sensitive area of the sensor 214. On account of the small-area focus, it is possible for the sensor 214 to have a comparatively small detection area. By way of example, the sensor 214 may have a detection area of less than 0.1 mm$^2$. Preferably, the sensor 214 has a detection area of less than 0.05 mm$^2$. Particularly preferably, the sensor 214 has a detection area of less than 0.02 mm$^2$. However, the sensor may also have a larger detection area, e.g. larger than 0.1 mm$^2$ or larger than 10 mm$^2$ or larger than 100 mm$^2$. The sensor may be a pixelated sensor. Thus, the focusing optical unit 213 is configured to focus the beam path 291 of the specific spectral portion of the light onto the detection area of the sensor 214.

This may be effected in very different ways. By way of example, the focusing optical unit 213 may comprise a number of mirrors. The mirrors may have a suitable focal length such that focusing is achieved. In particular, a particularly achromatic implementation may be achieved as a result thereof, as mirrors are used instead of lenses. On the other hand, a structure may be comparatively complex and a large number of elements, such as e.g. deflection mirrors, may be necessary.

Figure 3:
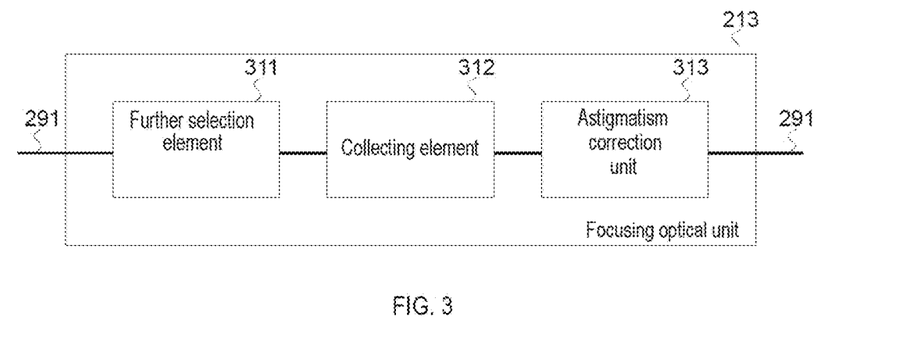
FIG. 3 is a schematic view of the focusing optical unit of FIG. 2 in greater with the focusing optical unit comprising a transverse chromatic aberration correction element, a collecting element and an astigmatism correction unit.

FIG. 3 depicts a specific implementation of the focusing optical unit 213. It is obvious from FIG. 3 that the focusing optical unit 213 comprises a transverse chromatic aberration correction element 311, a collecting element 312 and an astigmatism correction unit 313. The transverse chromatic aberration correction element 311, the collecting element 312 and the astigmatism correction unit 313 are arranged in the beam path 291 of the specific spectral portion of the light in the sequence as specified, proceeding from the selection element 212. By way of example, the transverse chromatic aberration correction element 311 may be provided, in particular, when the selection element 212 comprises one or more wedge-shaped prisms. By way of example, provision of the transverse chromatic aberration correction element 311 may be dispensed with provided that the selection element 212 comprises no wedge-shaped prism and is implemented, for example, by a angled mirror. The transverse chromatic aberration correction element 311 and the selection element 212 are arranged relative to one another in such a way that a transverse chromatic aberration of the selection element 212 counteracts a further transverse chromatic aberration of the transverse chromatic aberration correction element 311. What this may achieve is a reduction or compensation of the transverse chromatic aberration caused by the selection element 212 by way the transverse chromatic aberration correction element 311.

As explained above, the dispersive element 211 provides a spectral decomposition of the beam path 290 of the light. The collecting element. 312 may accordingly bring about a spectral unification of the beam path 291 of the spectral portion of the light. The collecting element 312, may be implemented e.g. as prism and/or grating in accordance with the dispersive element 211.

The focusing optical unit 213 furthermore comprises the astigmatism correction unit 313. The astigmatism correction unit 313 is configured to reduce an astigmatic aberration of the beam path 291 of the spectral portion of the light. To this end, the astigmatism correction unit 313 may comprise a tilted plane parallel plate and/or decentered lenses. The fundamentals of corresponding astigmatism correction units are known to a person skilled in the art, and so no further details need to be provided here.

Figure 4:
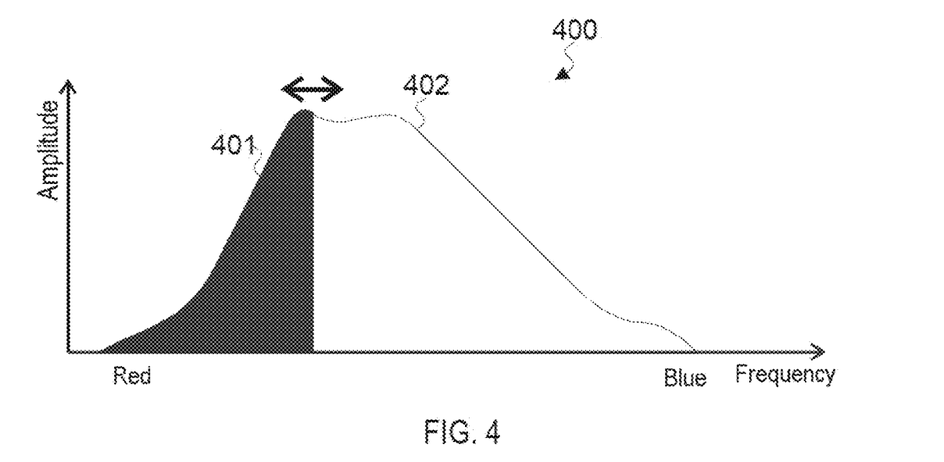
FIG. 4 illustrates a spectral portion.

FIG. 4 illustrates the spectrum 400 of the light, as it is e.g. guided to the detector device 113 from the specimen HI An edge region of the spectrum 400 is highlighted as spectral portion 401. By way of the selection element 212 it is possible to select this spectral portion 401 or separate the latter from the further spectral portion 402 which is complementary thereto. A sharpness of the separation of the spectral portions 401, 402 is denoted by the spectral resolution.

Figure 5:
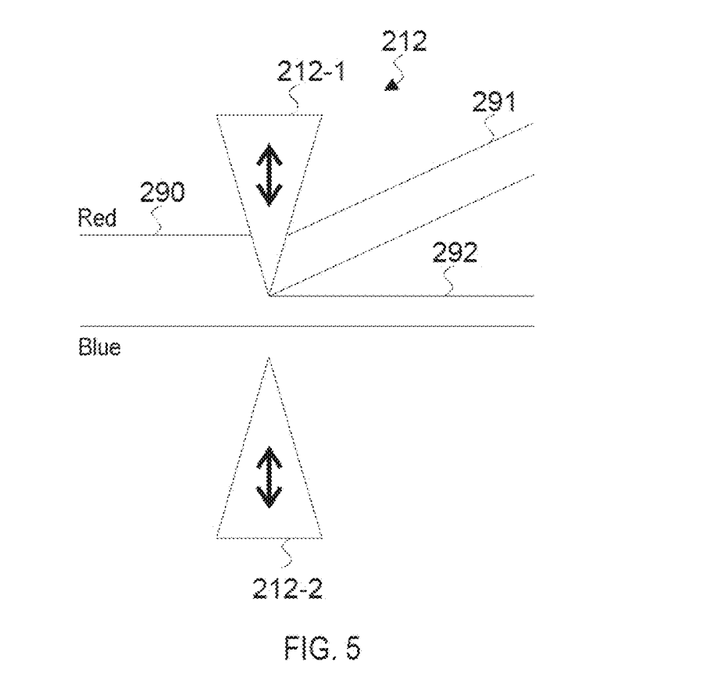
FIG. 5 is a schematic view of the selection element of FIG. 2 in greater detail, with the selection element comprising two wedge-shaped prisms.

This selection is illustrated in FIG. 5 for implementation of the selection element 212 as pair of wedge-shaped prisms 212-1, 212-2. The beam path of the light 290 is incident on the selection element 212 from the left. The upper wedge-shaped prism 212-1 protrudes into the beam path 290, while the lower wedge-shaped prism 212-2 does not protrude into the beam path 290. Since the selection element 212 is situated at a point in the beam path 290 of the light downstream of the dispersive element 211 (cf. FIG. 2), the region of the beam path 290 into which the upper wedge-shaped prism 212-1 protrudes (does not protrude) corresponds to the spectral portion 401 (the further spectral portion 402). As a result, the spectral portion 401 and the further spectral portion 402 are separated; the beam path 290 of the light is split into the beam path 291 of the spectral portion 401 and the beam path 292 of the further portion 402. In particular, the beam path 291 of the spectral portion 401 and the beam path 292 of the further spectral portion 402 are separated from the beam path 290 of the light.

By way of example, the selection element 212 could comprise further prisms (not shown in FIG. 5). As a result, it is possible to separate beam paths for further spectral portions.

In principle, it is possible to provide the sensor 214 for the beam path 291 of the portion 401 of the light or for the beam path 292 of the further spectral portion 402 of the light. It would also be possible to provide a plurality of sensors 214, namely respectively one for each beam path 291, 292 of the spectral portions 401, 402. Referring to FIG. 2, this may mean that the detector device 113 furthermore comprises the further focusing optical unit arranged downstream of the selection element 212 in the beam path 292 of the further spectral portion 402 of the light, wherein the further focusing optical unit is configured to focus the beam path 292 of the further spectral portion 402 of the light onto the further sensor.

As explained above, the beam path 291 of the spectral portion 401 of the light passes through the wedge-shaped prism 212-1 of the selection element 212. This results in the transverse chromatic aberration for the beam path 291 of the spectral portion 401 of the light. The transverse chromatic aberration correction element 311 is provided for compensating the transverse chromatic aberration; see FIG. 6. The transverse chromatic aberration correction element 311 also comprises a pair of wedge-shaped prisms 311-1, 311-2, 11 is clear from FIG. 6 that the wedge-shaped prisms 212-1, of the selection element 212 and the wedge-shaped prisms 311-1, 311-2 of the transverse chromatic aberration correction element 311 are arranged in a manner complementary to one another with respect to the beam path 291 of the spectral portion 401 of the light. As a result, it is possible to compensate the transverse chromatic aberration caused by passing through the wedge-shaped prism 212-1 of the selection element 212 by passing through the wedge-shaped prism 311-1 of the transverse chromatic aberration correction element 211. To this end, the material of the prisms 212-1, 21.2-2 of the selection element 212 is the same as the material of the prisms 311-1, 311-2 of the transverse chromatic aberration correction element 311. Further, the wedge angle of the prisms 212-1, 212-2 of the selection element 212 is the same as the wedge angle of the prisms 311-1, 311-2 of the transverse chromatic aberration correction element 311.

Figure 6:
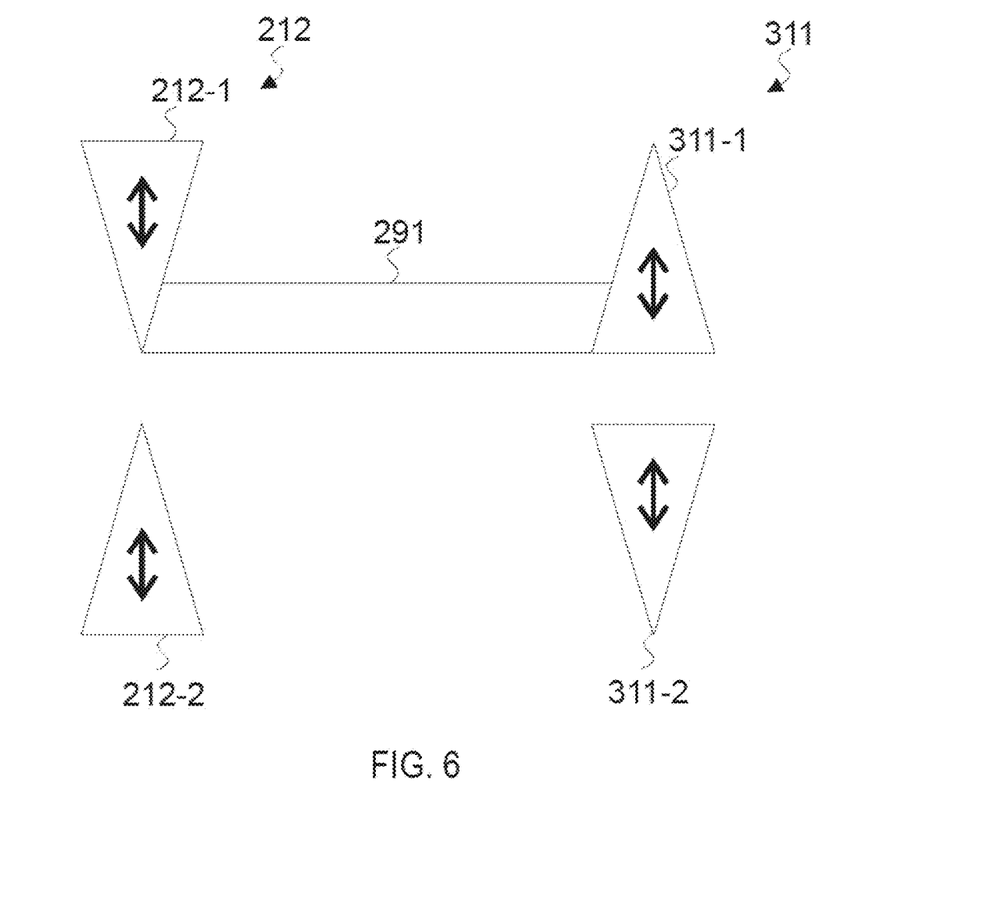
FIG. 6 illustrates the coupled displaceable positioning of the selection element of FIG. 5 and of the transverse chromatic aberration correction element of FIG. 3, with the transverse chromatic aberration correction element comprising two wedge-shaped prisms.

It is clear from FIGS. 5 and 6 that the selection element 212 and the transverse chromatic aberration correction element 311 are arranged in a movable fashion. To this end, the detector device 113 comprises a drive unit configured to position the selection element 212 in a displaceable manner in the beam path 290 of the light and to position the transverse chromatic aberration correction element 311 in a displaceable manner in the beam path 291 of the spectral portion 401 of the light (indicated by the vertical arrows in the FIGS. 5 and 63. A position of the wedge-shaped prism 212-1 of the selection element 212 which protrudes further (less far) into the beam path 290 of the light causes the spectral portion 401 separated from the beam path 290 of the light by the selection element 212 to be broader (less broad); cf. FIG. 4. As a result, the spectral portion 401 may be flexibly dimensioned. By means of the drive unit, it is further possible to completely remove the upper wedge-shaped prism 212-1 of the selection element 212 from the beam path 290 of the light; at the same time, the lower wedge-shaped prism 212-2 may be positioned in such a way that it at least partly protrudes into the beam path 290 of the light. This allows a spectral portion to be selected at the other end of the spectrum 400 of the light.

Thus, by means of the above-described techniques, it is possible to flexibly select the spectral portion 401 selected by the selection element 212. In order to obtain the transverse chromatic aberration being reduced to the best possible extent for the various positions of the selection element 212 at the same time, the drive unit is configured to position the selection element 212 and the transverse chromatic aberration correction element 311 in a coupled manner. By way of example, if the upper prism 212-1 of the selection element 212 is repositioned by a certain distance, the upper prism 311-1 of the transverse chromatic aberration correction element 311 may be repositioned by the same certain distance.

Figure 7:
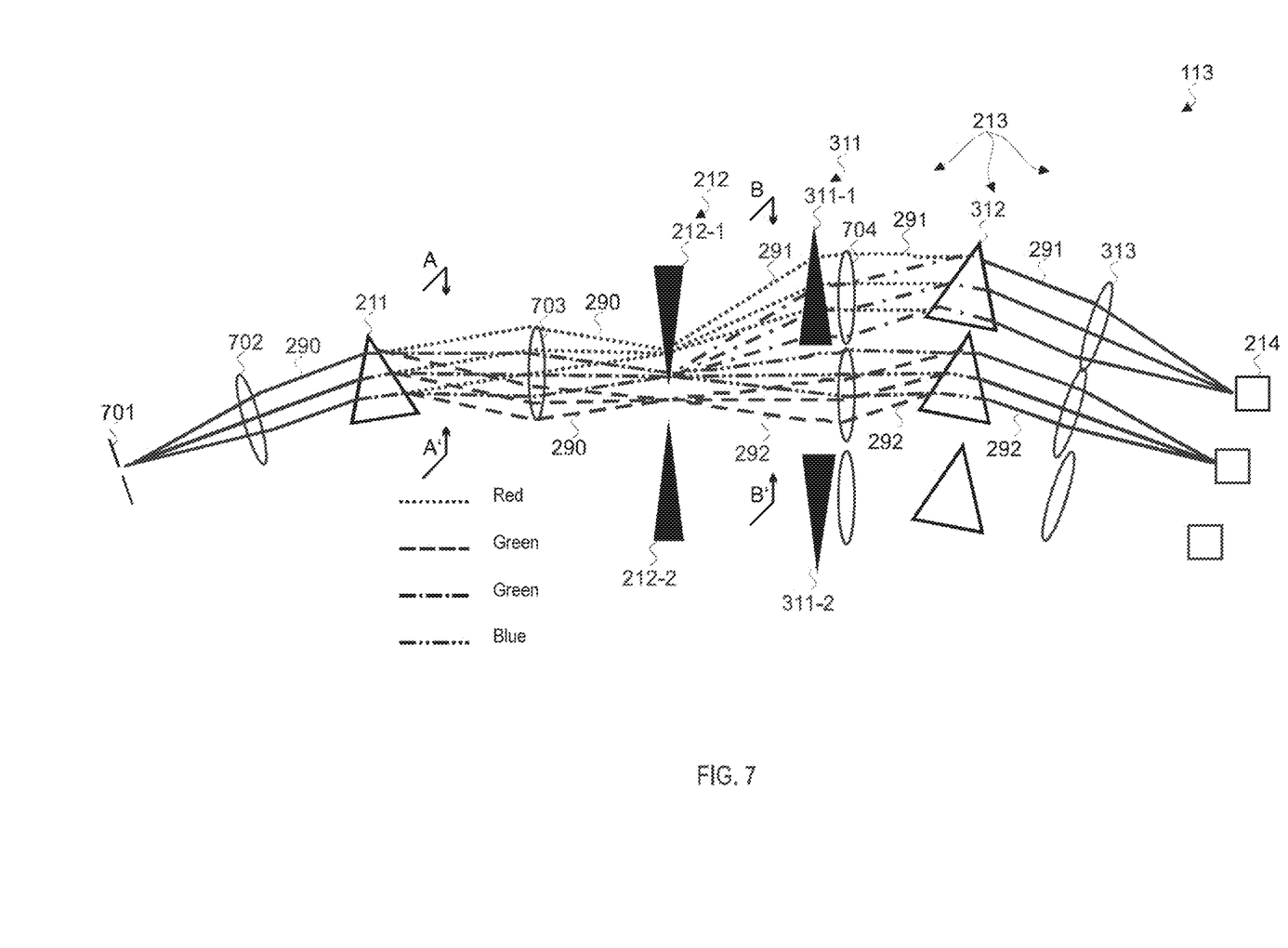
FIG. 7 is a schematic view of a detector device in accordance with various embodiments.

FIG. 7 illustrates the detector device 113 in accordance with various embodiments with particularly high levels of detail, in particular, various colors of the light are illustrated using different lines (red: dotted: green: dashed and dash-dotted; blue: dash-dot-dotted; non-spectrally-separated light is illustrated using full lines).

The light is obtained through a pinhole 701. A lens 702 is provided for parallelizing the beam path 290. Then, the beam path 290 of the light passes through the dispersive element 211 which, in the scenario of FIG. 7, is embodied as a wedge-shaped prism. The dispersive prism provides a decomposition of the beam path 290 of the light into the various spectral components. Here, a red component of the spectrum 400 (depicted using the dotted line in FIG. 7) is refracted less strongly than a green component of the spectrum 400 (depicted using the dashed and dot-dashed lines in FIG. 7) and a blue component of the spectrum 400 (depicted using the dash-drat-dotted line in FIG. 7). Thus, the beam path 290 of the light is spread into the spectral components.

It is clear from FIG. 7 that the selection element 212 provides a split of the beam path 290 of the light into the beam path 291 of the spectral portion 401 at the red edge of the spectrum 400 and into the beam path 292 of the further spectral portion 402 at the blue edge of the spectrum 400. The separation of the spectral portion 401 from the further spectral portion 402 occurs in the green range of the spectrum 400 therefore, two green spectral components are depicted in FIG. 7 beyond the selection element 212, said green spectral components respectively being arranged on both sides of the separation of the spectral portions 401, 402.

FIG. 7 also illustrates the transverse chromatic aberration correction element 311 which provides the correction of the transverse chromatic aberration caused by the selection element 212.

The spectral decomposition of the beam paths 291, 292 is compensated by the collecting element 312. In FIG. 7, the collecting element 312 is configured as a wedge-shaped prism. The collecting element 312 provides a spectral unification of the beam paths 291, 292.

The detector device 113 furthermore comprises an imaging optics in the form of two lenses 703, 704. The lenses 703, 704 are arranged in the beam path 290 of the light and in the beam path 291 of the spectral portion 401 of the light between the dispersive element 211 and the collecting element 312 and bring about optical imaging of the dispersive element 211 onto the collecting element 312. As a result, there can be particularly good spectral unification of the beam paths 291, 297.

In particular, the selection element 212 may be situated in a focal plane of the imaging optics 113. As a result, a particularly high spectral resolution may be achieved. The beam path 290 of the light is split in a line-shaped manner in the focal plane.

Furthermore, the astigmatism correction unit 313 is provided upstream of the sensor 214. The astigmatism correction unit 313 is depicted in a simplified manner in FIG. 7 and may, for example, comprise a tilted plane parallel plate (not shown in FIG. 7).

Three collecting elements 312 and three astigmatism correction units 313 and three sensors 214 are respectively provided in the scenario of FIG. 7. In principle, this allows light to be detected separately for three spectral portions. A larger number of spectral portions could also be detected separately.

The sensor 214 may be configured in very different ways. The sensor may have an unstructured sensitive area. Alternatively, the sensor may also comprise a ring structure. Then, the sensor 214 itself may serve as an electronic pinhole. The electronic pinhole may be matched to the respective spectral portion 401, 402 which is intended to be detected. As a result, each sensor 214 may form a dedicated pinhole. The stop effect of the pinhole 701 is obtained by the structuring of the sensor 214. Then, provision of the pinhole 701 may be dispensed with.

Figure 8:
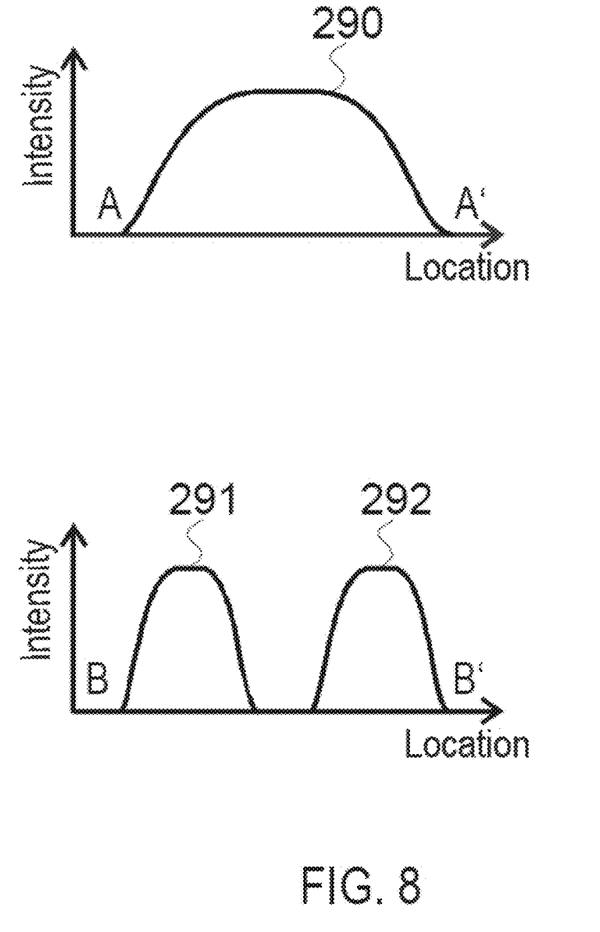
FIG. 8 illustrates the spectral spread of the beam path of the light and the separation of the beam path of the spectral portion of the light.

FIG. 8 depicts the intensity of the beam path 290 of the light as a function of the location along the axis A-A' (cf. FIG. 7) and the intensity of the beam path 291 of the spectral portion 401 of the light as a function of the location along the axis B-B' (cf. FIG. 7). It is clear from FIG. 8 that the dispersive element 211 provides a spread of the beam path 290 of the light into the various spectral components, but it does not bring about a separation. The separation is achieved by the selection element 212; the beam path 291 of the spectral portion 401 of the light has well-defined edges.

FIG. 7 is a schematic sketch. By way of example, use could be made of corresponding techniques for confocal microscopy, which are parallelized perpendicular to the plane of the drawing in FIG. 7.

Figure 9:
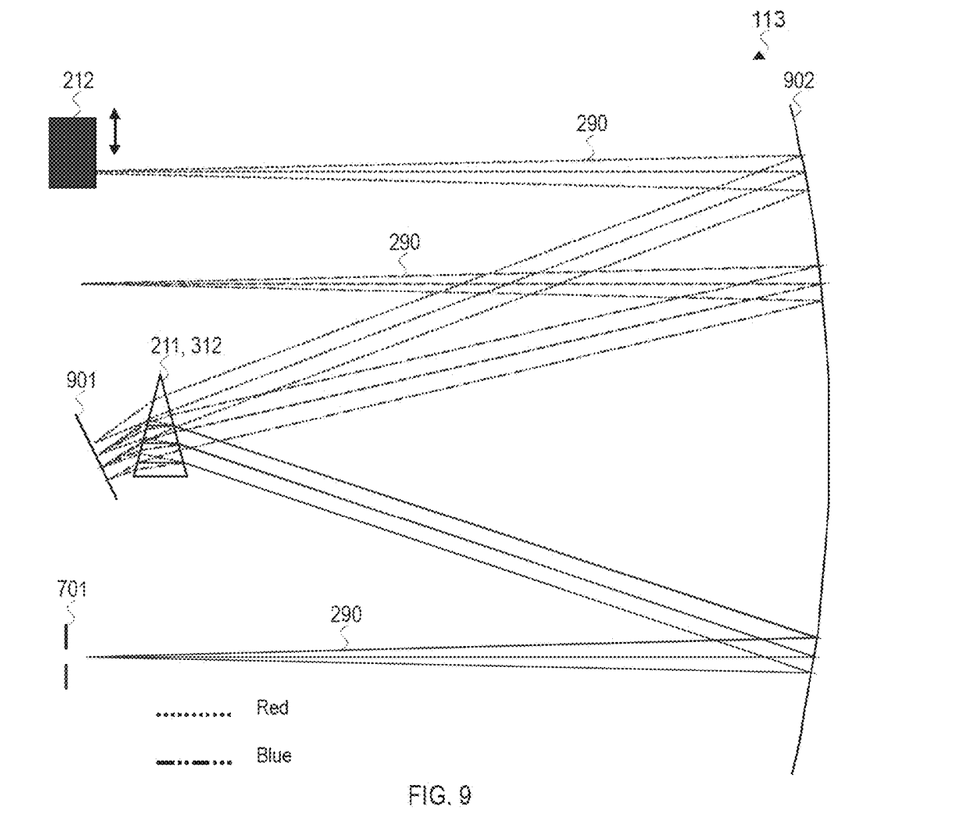
FIG. 9 is a schematic view of a detector device in accordance with various embodiments, with FIG. 9 being a side view.
Figure 10:
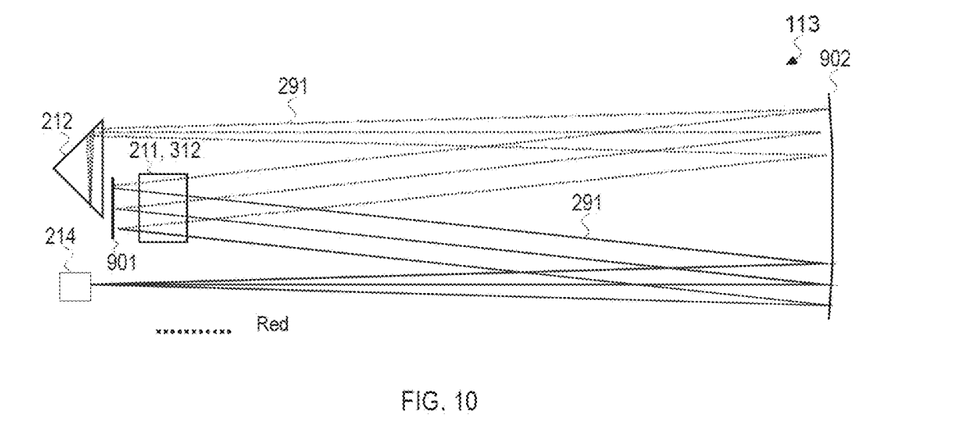
FIG. 10 is a schematic view of the detector device of FIG. 9, with FIG. 10 being a top view.

FIGS. 9 and 10 illustrate implementation of the invention in which mirrors 901, 902 are used as an imaging optics instead of lenses. Further, both the dispersive element 211 and the collecting element 312 are implemented by a single prism, through which both the beam path 290 of the light and the beam path 291 of the spectral portion 401 of the light pass. In this scenario of FIGS. 9 and 10, the selection element 212 is implemented as a angled mirror, and so a transverse chromatic aberration correction element may be dispensed with.

FIG. 9 initially illustrates a side view of the detector device 113. The beam path 290 of the light enters through the pinhole 701 and is guided via a mirror 902 onto the dispersive element 211. There, the spread into the various spectral components takes place. For reasons of clarity, only the red spectral component (dotted line) and the blue spectral component (dash-dot-dotted line) are depicted in FIG. 9.

The selection element 212, which is configured as an angled mirror, is disposed downstream of the dispersive element 211 in the beam path 290 of the light. It is clear from FIG. 9 that the selection element 212 only influences the red spectral component of the beam path 290 of the light and not the blue spectral component of the beam path 290 of the light; as a result, the spectral portion 401 is selected and separated from the beam path 290 of the light. The selection element 212 only protrudes partly into the beam path 290 of the light.

The angled mirror of the selection element 212 reflects the beam path 291 of the spectral portion 401 of the light (the beam path 291 of the spectral portion 401 of the light is not depicted in FIG. 9 for reasons of clarity).

The beam path 291 of the spectral portion 401 of the light is depicted in a top view in FIG. 10 (FIG. 10 in turn does not depict the beam path 290 of the light for reasons of clarity). It is clear from FIG. 10 that the beam path 291 of the spectral portion 401 of the light once again passes through the prism of the dispersive element 211; the effect of the collecting element 312 is obtained by this prism in this way. Then, the beam path is incident on the sensor 214.

By way of example, it would be possible furthermore to arrange the astigmatism correction unit 313 (not shown in FIGS. 9 and 10) in the beam path 291 of the spectral portion 401 of the light. However, using the astigmatism correction unit 313 may be dispensed with in the present case, as no prisms are used as selection element. However, should an astigmatic aberration occur as a result of the employed concave mirror, the astigmatism correction unit 313 may be configured to correct this aberration.

The detector device 113 comprises one selection element 212 in the scenario of FIG. 9. However, it would be possible for the detector device 113 to comprise more than one selection element 212. By way of example, a plurality of selection elements could be arranged in the beam path 290 in succession, in this way, a plurality beam paths 291 could be selected for the various spectral portions 401 and be separated from the beam path 290 of the light. By way of example, a corresponding statement also applies to the scenario in FIG. 7, where two selection elements 212 are already present.

It goes without saying that the features of the above-described embodiments and aspects of the invention may be combined with one another, in particular, the features may be used not only in the combinations described, but also in other combinations or by themselves, without departing from the field of the invention.

By way of example, in respect of the figures, it was predominantly scenarios in which one or two spectral portion(s) are selectively detected that were discussed—it was predominantly scenarios in which a selection element is present far the spatial separation of the corresponding beam path that were discussed. However, in accordance with various embodiments, it would also be possible for the detection device to comprise more than one selection element. By way of example, the detection device may comprise two or more selection devices. Accordingly, it may be possible to selectively detect more than one spectral portion.

The techniques described above may also be used for e.g. parallelized confocal microscopes. By way of example, a corresponding confocal microscope may be parallelized perpendicular to the beam paths predominantly discussed herein.

What is claimed is:

1. A detector device for a microscope, wherein the detector device comprises:
    a dispersive element in the beam path of the light;
    a selection element, wherein the selection element is arranged downstream of the dispersive element in a beam path of the light in such a way that it separates a beam path of a spectral portion of the light from the beam path of the light;
    a focusing optical unit arranged downstream of the selection element in the beam path of the spectral portion of the light, wherein the focusing optical unit is configured to focus the beam path of the spectral portion of the light onto a sensor arranged downstream of the focusing optical unit in the beam path of the spectral portion of the light; and
    a drive unit configured to position the selection element in a displaceable manner in the beam path of the light.

2. The detector device as claimed in claim 1,
    wherein the focusing optical unit comprises a transverse chromatic aberration correction element arranged in the beam path of the spectral portion of the light,
    wherein the selection element comprises at least one wedge-shaped prism,
    wherein the transverse chromatic aberration correction element comprises at least one wedge-shaped prism, and
    wherein the selection element and the transverse chromatic aberration correction element are arranged relative to one another in such a way that a transverse chromatic aberration of the at least one wedge-shaped prism of the selection element counteracts a further transverse chromatic aberration of the at least one wedge-shaped prism of the transverse chromatic aberration correction element.

3. The detector device as claimed in claim 2,
    wherein the at least one wedge-shaped prism of the selection element and the at least one wedge-shaped prism of the transverse chromatic aberration correction element are arranged complementary to one another with respect to the beam path of the spectral portion of the light.

4. The detector device as claimed in claim 3,
    wherein a material of the at least one prism of the selection element corresponds to a material of the at least one prism of the transverse chromatic aberration correction element, and/or
    wherein a wedge angle of the at least one prism of the selection element corresponds to a wedge angle of the at least one prism of the transverse chromatic aberration correction element.

5. The detector device as claimed in claim 2, wherein the drive unit is furthermore configured to position the transverse chromatic aberration correction element in a displaceable manner in the beam path of the spectral portion of the light, and wherein the drive unit is configured to position the selection element and the transverse chromatic aberration correction element in a coupled manner.

6. The detector device as claimed in claim 1, wherein the focusing optical unit comprises a collecting element arranged upstream of the sensor in the beam path of the spectral portion of the light, wherein the dispersive element is at least one of a prism and a grating, wherein the collecting element is at least one of a prism and a grating, wherein the dispersive element provides a spectral decomposition of the beam path of the light, and wherein the collecting element provides a spectral unification of the beam path of the spectral portion of the light.

7. The detector device as claimed in claim 6, wherein the detector device furthermore comprises an imaging optics arranged at least in part between the dispersive element and the collecting element in the beam path of the light and in the beam path of the spectral portion of the light, and wherein the imaging optics is configured to obtain optical imaging of the dispersive element onto the collecting element.

8. The detector device as claimed in claim 1, wherein the focusing optical unit comprises an astigmatism correction unit configured to reduce an astigmatic aberration of the beam path of the spectral portion of the light.

9. The detector device as claimed in claim 1, wherein the selection element is arranged in the beam path of the light in such a way that it separates a beam path of the further spectral portion of the light from the beam path of the light, wherein the detector device furthermore comprises a further focusing optical unit arranged downstream of the selection element in the beam path of the further spectral portion of the light, wherein the further focusing optical unit is configured to focus the beam path of the further spectral portion of the light onto a further sensor, and wherein the further sensor is arranged downstream of the further focusing optical unit in the beam path of the further spectral portion of the light.

10. The detector device as claimed in claim 1,
    wherein the sensor has a sensitive area of less than 0.1 mm2, preferably of less than 0.05 mm2, particularly preferably of less than 0.02 mm2, and
    wherein the focusing optical unit is configured to focus the beam path of the spectral portion of the light onto the sensitive area of the sensor.

11. The detector device as claimed in claim 1, wherein the sensor comprises a plurality of pixels configured to measure a focal distribution of the spectral portion of the light in a spatially resolved manner.

12. The detector device as claimed in claim 1, wherein the selection element comprises at least one angled mirror.

13. A microscope comprising a detector device as claimed in claim 1.

14. The microscope as claimed in claim 13, wherein the microscope is a confocal microscope.

15. The detector device as claimed in claim 1, wherein the sensor is configured to perform a spatially-resolved detection of a point spread function of the detector device.

16. The detector device as claimed in claim 1, wherein the drive unit is configured to position the selection element in the displaceable manner to select the spectral portion from a plurality of spectral portions.

* * * * *

UNITED STATES PATENT AND TRADEMARK OFFICE
CERTIFICATE OF CORRECTION

Page 1 of 2

PATENT NO. : 10,371,574 B2
APPLICATION NO. : 16/170931
DATED : August 6, 2019
INVENTOR(S) : Shafer et al.

It is certified that error appears in the above-identified patent and that said Letters Patent is hereby corrected as shown below:

In the Specification

Column 3, Line 38, please change "spatially resolved" to -- spatially-resolved --.

Column 4, Line 57, please change "one of prism" to -- one prism --.

Column 8, Line 8, please change "greater with" to -- greater detail, with --.

Column 10, Line 3, please change "tight." to -- light. --.

Column 10, Line 15, please change "a angled" to -- an angled --.

Column 10, Line 60, please change "a angled" to -- an angled --.

Column 11, Line 5, please change "element. 312" to -- element 312 --.

Column 11, Line 20, please change "HI An" to -- 112. An --.

Column 12, Line 4, please change "311-2, 11 is" to -- 311.2. It is --.

Column 12, Line 15, please change "211." to -- 311. --.

Column 12, Line 16, please change "21.2-2" to -- 212-2 --.

Column 12, Line 32, please change "63." to -- 6. --.

Column 13, Line 41, please change "297." to -- 292. --.

Signed and Sealed this
Thirty-first Day of December, 2019

Andrei Iancu
*Director of the United States Patent and Trademark Office*

CERTIFICATE OF CORRECTION (continued)
U.S. Pat. No. 10,371,574 B2

Column 14, Line 22, please change "a angled" to -- an angled --.

Column 15, Line 17, please change "far" to -- for --.